United States Patent
Higgins et al.

(10) Patent No.: US 9,435,784 B2
(45) Date of Patent: Sep. 6, 2016

(54) METHODS FOR DETECTING FILM FORMATION POTENTIAL IN FOOD PRODUCTS

(71) Applicant: Nestec S.A., Vevey (CH)

(72) Inventors: Leigh Anne Higgins, Grant, MI (US); Vivek Gnanasekharan, Jersey City, NJ (US)

(73) Assignee: Nestec S.A., Vevey (CH)

( * ) Notice: Subject to any disclaimer, the term of this patent is extended or adjusted under 35 U.S.C. 154(b) by 516 days.

(21) Appl. No.: 14/145,541

(22) Filed: Dec. 31, 2013

(65) Prior Publication Data

US 2014/0244201 A1    Aug. 28, 2014

Related U.S. Application Data

(60) Provisional application No. 61/770,698, filed on Feb. 28, 2013, provisional application No. 61/863,456, filed on Aug. 8, 2013.

(51) Int. Cl.
*G01D 3/00* (2006.01)
*G01N 33/10* (2006.01)

(52) U.S. Cl.
CPC .................................... *G01N 33/10* (2013.01)

(58) Field of Classification Search
CPC B65D 75/366; B65D 81/264; B65D 81/267; B65D 81/3446; B65D 65/42; B65D 81/28; B65D 1/34; B65D 2203/10; B65D 2207/00; B65D 2301/10; G06Q 30/02; A23G 3/346; A23G 2200/08; A23G 1/44; A23G 1/46; A23G 3/36; A23G 3/44; A23G 3/46; A23G 4/14; A23G 4/16
See application file for complete search history.

(56) References Cited

U.S. PATENT DOCUMENTS

| 4,167,867 A | 9/1979 | Bischoff et al. |
| 2005/0136161 A1* | 6/2005 | Okita .................... A23L 3/36 |
| | | 426/393 |
| 2006/0121165 A1* | 6/2006 | Morris ................. B65D 79/02 |
| | | 426/383 |

FOREIGN PATENT DOCUMENTS

WO    2012093326 A1    7/2012

OTHER PUBLICATIONS

International Search Report and Written Opinion from corresponding PCT patent application No. PCT/IB2013/061459 dated Apr. 16, 2014.
B. Fu, T.P. Labuza, Section IV, Monitoring of Quality in Frozen Foods, "Chapter 19, Shelf Life Testing: Procedures and Prediction Methods, 19.5 Accelerated Shelf-Life Testing," In: Marilyn Erickson, "Quality in Frozen Food," Springer, Nov. 30, 1997, pp. 377-415.

* cited by examiner

*Primary Examiner* — Roy Y Yi
(74) *Attorney, Agent, or Firm* — Gary M. Lobel, Esq.

(57) ABSTRACT

The present disclosure provides methods for determining the film forming potential of food products. In a general embodiment, a method for determining the film forming potential of a food product is provided and includes providing a temperature-control device having a processor and a computer readable medium storing instructions which, when executed, cause the processor to cycle an interior temperature of the temperature-control device between different temperatures in a predetermined amount of time. The methods further include placing a packaged food product in the temperature-control device, and causing the processor to execute the stored instructions.

20 Claims, No Drawings

METHODS FOR DETECTING FILM FORMATION POTENTIAL IN FOOD PRODUCTS

BACKGROUND

The present disclosure relates generally to food technology. More specifically, the present disclosure relates to methods for detecting film formation potential in food products packaged in various types of packages including, for example, glass jars and plastic containers.

It is common in the food industry to store packaged food products in a warehouse prior to shipping of the products to retail stores. In this regard, food products are manufactured and packaged in individual containers such as glass jars or plastic containers before being packaged in bulk for distribution to retail stores. Depending on factors such as retail demand or shipping schedules, the packaged food products may sit in a warehouse for a significant amount of time. Typically, however, packaged food products may sit in a warehouse, or on a delivery truck during transport, for at least several days. During this time period, the warehouse temperatures can fluctuate wildly between warm and cool temperatures, which often correspond to daytime and nighttime temperatures, respectively. For example, a warehouse in a warm temperature climate may have a widely varying temperature range in a twenty-four hour period including very warm temperatures during the day and very cool temperatures at night.

Although such temperature changes generally do not affect the edibility of the products, cyclic changes in temperature (either losses or gains of temperature) can cause issues with product quality management. For example, temperature cycling between warm and cool temperatures can cause a film to form on either or both of the product surface or the interior lid surface. Although the product may still be consumed, the films are rather unsightly and can invoke a feeling of poor product quality in the mind of the consumer. If the consumer is sufficiently turned-off by the aesthetics of the product, the consumer may refuse to buy any further food products manufactured by the brand and/or may have negative feelings about all products manufactured by the brand. Accordingly, such unacceptable product quality could be a costly problem for food product manufacturers.

Therefore, there exists a need for methods that are able to detect film formation potential in food products.

SUMMARY

In the present disclosure, methods for detecting film formation potential in food products are provided. In an embodiment, methods for testing a food product include providing a temperature-control device having a processor and a computer readable medium storing instructions which, when executed, cause the processor to cycle an interior temperature of the temperature-control device between at least three temperatures in a predetermined amount of time. The methods further include placing a packaged food product in the temperature-control device, and causing the processor to execute the stored instructions.

In another embodiment, methods for detecting film formation potential are provided. The methods include providing a temperature-control device having a processor and a computer readable medium storing instructions which, when executed, cause the processor to cycle an interior temperature of the temperature-control device between at least three temperatures in a predetermined amount of time. The methods further include placing a packaged food product in the temperature-control device, and causing the processor to execute the stored instructions.

In an embodiment, the methods further include programming the computer readable medium to contain the stored instructions. The methods may also include shearing the packaged food product before packaging.

In an embodiment, the stored instructions, when executed, cause the processor to cycle the interior temperature of the temperature-control device more than once.

In an embodiment, a second cycle by the processor cycles the interior temperature of the temperature-control device between the at least three temperatures.

In an embodiment, a second cycle by the processor cycles the interior temperature of the temperature-control device between the at least three temperatures, wherein at least one of the two temperatures of the second cycle is different from each of the at least three temperatures.

In an embodiment, the packaged food product includes starch, which can be native, or added, or combinations thereof.

In an embodiment, the temperature-control device is an incubator.

In an embodiment, the packaged food product is a food product selected from the group consisting of pudding, baby food, soup, or combinations thereof.

In an embodiment, the predetermined amount of time ranges from about 6 hours to about 18 hours, or from about 8 hours to about 16 hours, or from about 10 hours to about 14 hours, or about 12 hours.

In an embodiment, a first and a third temperature are the same temperature. Alternatively, a first and a third temperature may be different temperatures.

In an embodiment, a second temperature is higher than the first and the third temperatures.

In an embodiment, the methods further include providing a second packaged food product having a composition that is different than the packaged food product, placing the second packaged food product in the temperature-control device, and causing the processor to execute the stored instructions.

In an embodiment, the packaged food product includes starch, and the second packaged food product has an amount of starch that is different from an amount of starch in the packaged food product.

In an embodiment, the packaged food product includes starch, and the second packaged food product has a type of starch that is different from the starch in the packaged food product.

In an embodiment, the methods further include holding the interior temperature of the temperature-control device at any one of the at least three temperatures for a predetermined amount of time.

In an embodiment, the methods further include removing the packaged food product from the temperature-control device after the cycling.

In an embodiment, the methods further include determining an amount of film formed on a surface selected from the group consisting of the food product, an interior lid on the packaged food product, or combinations thereof.

In yet another embodiment, methods for operating an incubator are provided. The methods include providing an incubator having a processor and a computer readable medium storing instructions which, when executed, cause the processor to cycle an interior temperature of the incubator between at least three temperatures in a predetermined amount of time. The methods further include placing a packaged food product in the incubator, and causing the processor to execute the stored instructions.

In an embodiment, the methods further include programming the computer readable medium to contain the stored instructions.

In an embodiment, the methods further include shearing the packaged food product before packaging.

In an embodiment, the stored instructions, when executed, cause the processor to cycle the interior temperature of the incubator more than once.

In an embodiment, a second cycle by the processor cycles the interior temperature of the incubator between the at least three temperatures.

In an embodiment, a second cycle by the processor cycles the interior temperature of the incubator between three temperatures, wherein at least one of the three temperatures of the second cycle is different from each of the at least three temperatures.

In an embodiment, the packaged food product includes starch.

In an embodiment, the incubator includes an input device configured for modifying the stored instructions.

In an embodiment, the packaged food product is a food product selected from the group consisting of pudding, baby food, soup, or combinations thereof.

In an embodiment, the predetermined amount of time ranges from about 6 hours to about 18 hours, or from about 8 hours to about 16 hours, or from about 10 hours to about 14 hours, or about 12 hours.

In an embodiment, a first and a third temperature are the same temperature. Alternatively, a first and a third temperature may be different temperatures.

In an embodiment, a second temperature is higher than the first and the third temperatures.

In an embodiment, the methods further include providing a second packaged food product having a composition that is different than the packaged food product, placing the second packaged food product in the incubator, and causing the processor to execute the stored instructions.

In an embodiment, the packaged food product includes starch, and the second packaged food product has an amount of starch that is different from an amount of starch in the packaged food product. Alternatively, the packaged food product does not include starch.

In an embodiment, the packaged food product includes starch, and the second packaged food product has a type of starch that is different from the starch in the packaged food product.

In an embodiment, the methods further include holding the interior temperature of the incubator at any one of the at least three temperatures for a predetermined amount of time.

In an embodiment, the methods further include removing the packaged food product from the incubator after the cycling.

In an embodiment, the methods further include determining an amount of film formed on a surface selected from the group consisting of the food product, an interior lid on the packaged food product, or combinations thereof.

In still yet another embodiment, methods for determining a film formation potential of a food product and provided. The methods include providing a temperature-control device having (i) a processor and (ii) a computer-readable medium accessible to the processor and containing instructions stored therein which, when executed, is programmed to cause the processor to increase an interior temperature of the temperature-control device to a first temperature in a first amount of time, and decrease the interior temperature of the temperature-control device to a second temperature in a second amount of time. The methods further include placing a packaged food product comprising starch in the temperature-control device, and causing the processor to execute the instructions.

In an embodiment, the methods further include programming the computer readable medium to contain the stored instructions.

In an embodiment, the methods further include shearing the packaged food product.

In an embodiment, the stored instructions, when executed, cause the processor to repeat the increase and decrease steps.

In an embodiment, the stored instructions, when executed, cause the processor to increase the interior temperature of the temperature-control device to a third temperature in a third amount of time, and decrease the interior temperature of the temperature-control device to a fourth temperature in a fourth amount of time.

In an embodiment, the third and fourth temperatures may be the same as, or different than, either of the first and second temperatures.

In an embodiment, the third and fourth amounts of time may be the same as, or different than, either of the first and second amounts of time.

In an embodiment, the temperature-control device is an incubator.

In an embodiment, the packaged food product is a food product selected from the group consisting of pudding, baby food, soup, or combinations thereof.

In an embodiment, the first amount of time ranges from about 2 hours to about 10 hours, or from about 4 hours to about 8 hours, or about 6 hours.

In an embodiment, the second amount of time ranges from about 2 hours to about 10 hours, or from about 4 hours to about 8 hours, or about 6 hours.

In an embodiment, the first and the second temperature are different temperatures.

In an embodiment, the methods further include providing a second packaged food product having a composition that is different than the packaged food product, placing the second packaged food product in the temperature-control device, and causing the processor to execute the stored instructions.

In an embodiment, the second packaged food product has an amount of starch that is different from an amount of starch in the packaged food product.

In an embodiment, the second packaged food product has a type of starch that is different from the starch in the packaged food product.

In an embodiment, the methods further include holding the interior temperature of the temperature-control device at the first temperature for a predetermined amount of time.

In an embodiment, the methods further include holding the interior temperature of the temperature-control device at the second temperature for a predetermined amount of time.

In an embodiment, the methods further include removing the packaged food product from the temperature-control device after executing the instructions.

In an embodiment, the methods further include determining an amount of film formed on a surface selected from the group consisting of the food product, an interior lid on the packaged food product, or combinations thereof.

In another embodiment, methods for determining a film formation potential of a food product are provided. The methods include providing a temperature-control device having (i) a processor and (ii) a computer-readable medium accessible to the processor and containing instructions stored therein which, when executed, cause the processor to ramp an interior temperature of the temperature-control device from a first temperature to a second temperature, and ramp the interior temperature of the temperature-control device from the second temperature to the first temperature. The methods further include placing a packaged food product comprising starch in the temperature-control device, and causing the processor to execute the instructions.

In an embodiment, the methods further include programming the computer readable medium to contain the stored instructions.

In an embodiment, the methods further include shearing the packaged food product.

In an embodiment, the stored instructions, when executed, cause the processor to repeat the increase and decrease steps.

In an embodiment, the stored instructions, when executed, cause the processor to increase the interior temperature of the temperature-control device to a third temperature in a third amount of time, and decrease the interior temperature of the temperature-control device to a fourth temperature in a fourth amount of time.

In an embodiment, the third and fourth temperatures may be the same as, or different than, either of the first and second temperatures.

In an embodiment, the third and fourth amounts of time may be the same as, or different than, either of the first and second amounts of time.

In an embodiment, the temperature-control device is an incubator.

In an embodiment, the packaged food product is a food product selected from the group consisting of pudding, baby food, soup, or combinations thereof.

In an embodiment, the first amount of time ranges from about 2 hours to about 10 hours, or from about 4 hours to about 8 hours, or about 6 hours.

In an embodiment, the second amount of time ranges from about 2 hours to about 10 hours, or from about 4 hours to about 8 hours, or about 6 hours.

In an embodiment, the first and the second temperature are different temperatures.

In an embodiment, the methods further include providing a second packaged food product having a composition that is different than the packaged food product, placing the second packaged food product in the temperature-control device, and causing the processor to execute the stored instructions.

In an embodiment, the second packaged food product has an amount of starch that is different from an amount of starch in the packaged food product.

In an embodiment, the second packaged food product has a type of starch that is different from the starch in the packaged food product.

In an embodiment, the methods further include holding the interior temperature of the temperature-control device at the first temperature for a predetermined amount of time.

In an embodiment, the methods further include holding the interior temperature of the temperature-control device at the second temperature for a predetermined amount of time.

In an embodiment, the methods further include removing the packaged food product from the temperature-control device after executing the instructions.

In an embodiment, the methods further include determining an amount of film formed on a surface selected from the group consisting of the food product, an interior lid on the packaged food product, or combinations thereof.

In yet another embodiment, methods for simulating warehouse storage conditions of a food product are provided. The methods include providing a temperature-control device having (i) a processor and (ii) a computer-readable medium accessible to the processor and containing instructions stored therein which, when executed, cause the processor to ramp an interior temperature of the temperature-control device from a first temperature to a second temperature to simulate daytime warehouse temperatures, and ramp the interior temperature of the temperature-control device from the second temperature to the first temperature to simulate nighttime warehouse temperatures. The methods further include placing a food product in the temperature-control device, and causing the processor to execute the instructions.

In an embodiment, the methods further include programming the computer readable medium to contain the stored instructions.

In an embodiment, the methods further include shearing the packaged food product.

In an embodiment, the stored instructions, when executed, cause the processor to repeat the increase and decrease steps.

In an embodiment, the stored instructions, when executed, cause the processor to increase the interior temperature of the temperature-control device to a third temperature in a third amount of time, and decrease the interior temperature of the temperature-control device to a fourth temperature in a fourth amount of time.

In an embodiment, the third and fourth temperatures may be the same as, or different than, either of the first and second temperatures.

In an embodiment, the third and fourth amounts of time may be the same as, or different than, either of the first and second amounts of time.

In an embodiment, the temperature-control device is an incubator.

In an embodiment, the packaged food product is a food product selected from the group consisting of pudding, baby food, soup, or combinations thereof.

In an embodiment, the first amount of time ranges from about 2 hours to about 10 hours, or from about 4 hours to about 8 hours, or about 6 hours.

In an embodiment, the second amount of time ranges from about 2 hours to about 10 hours, or from about 4 hours to about 8 hours, or about 6 hours.

In an embodiment, the first and the second temperature are different temperatures.

In an embodiment, the methods further include providing a second packaged food product having a composition that is different than the packaged food product, placing the second packaged food product in the temperature-control device, and causing the processor to execute the stored instructions.

In an embodiment, the second packaged food product has an amount of starch that is different from an amount of starch in the packaged food product.

In an embodiment, the second packaged food product has a type of starch that is different from the starch in the packaged food product.

In an embodiment, the methods further include holding the interior temperature of the temperature-control device at the first temperature for a predetermined amount of time.

In an embodiment, the methods further include holding the interior temperature of the temperature-control device at the second temperature for a predetermined amount of time.

In an embodiment, the methods further include removing the packaged food product from the temperature-control device after executing the instructions.

In an embodiment, the methods further include determining an amount of film formed on a surface selected from the group consisting of the food product, an interior lid on the packaged food product, or combinations thereof.

An advantage of the present disclosure is to provide improved methods for detecting film formation potential in packaged food products.

Yet another advantage of the present disclosure is to provide preprogrammed incubators for detecting film formation potential in packaged food products.

Still yet another advantage of the present disclosure is to provide methods for cycling temperatures to determine film formation potential in packaged food products.

Another advantage of the present disclosure is to provide methods for providing improved food products that do not experience film formation.

Additional features and advantages are described herein, and will be apparent from the following Detailed Description.

DETAILED DESCRIPTION

As used in this disclosure and the appended claims, the singular forms "a," "an" and "the" include plural referents unless the context clearly dictates otherwise.

As used herein, "about" is understood to refer to numbers in a range of numerals. Moreover, all numerical ranges herein should be understood to include all integer, whole or fractions, within the range.

As used herein, a "cycle" of temperature, or "cycling" temperatures, refers to the increase of a temperature from a first temperature to a second temperature, followed by a decrease of the temperature from the second temperature back to the first temperature.

As used herein, an "incubator" is understood to mean a device that is used to control and maintain optimal temperature and/or humidity, and/or other conditions (e.g., carbon dioxide and/or oxygen content of the atmosphere) inside. Such incubators are known in the art and are typically used to grow and maintain biological cultures. Examples of such incubators are incubators manufactured by the Darwin Chambers Company.

As used herein, a temperature "ramp" is understood to mean the rate of change in temperature over time, which is typically expressed in degrees per second.

It is common in the food industry to store packaged food products in a warehouse prior to shipping of the products to retail stores. In this regard, food products are manufactured and packaged in individual containers such as glass jars or plastic containers before being packaged in bulk for distribution to retail stores. Depending on factors such as retail demand or shipping schedules, the packaged food products may sit in a warehouse for a significant amount of time. Typically, however, packaged food products may sit in a warehouse for at least several days. During this time period, the warehouse temperatures can fluctuate between warm and cool temperatures that correspond to daytime and nighttime temperatures, respectively. For example, a warehouse in a warm temperature climate may have a widely varying temperature range in a twenty-four hour period including very warm temperatures during the day and cool temperatures at night.

Although such temperature changes generally do not affect the edibility of the products, cyclic changes in temperature (either losses or gains of temperature) can cause issues with product quality management. For example, temperature cycling between warm and cool temperatures can cause a film to form on either or both of the product surface or the interior lid surface. Although the product may still be consumed, the films are rather unsightly and can invoke a feeling of poor product quality in the mind of the consumer. If the consumer is sufficiently turned-off by the aesthetics of the product, the consumer may refuse to buy any further food products manufactured by the brand and/or may have negative feelings about all products manufactured by the brand. Accordingly, unacceptable product quality could be a costly problem for food product manufacturers.

More specifically, films can form on either or both of a food surface or on a lid surface of the container in which the food is housed. In this regard, a product surface film can form where a container lid is cool, and the container and food product are warm. Further, a container lid film can form where a container lid is warm, and the container and food product are cool. Potential reasons for such film formations will be discussed further below.

A main factor in film formation is evaporation of water from the food product into the headspace of the container between the product and the lid. This occurs when the vapor pressure of the loosely bound water in the product exceeds the pressure imposed upon it. Since vapor pressure increases with an increase in temperature, evaporation can continue until irreversibility occurs. Sometimes the water lost cannot be reabsorbed by the product and, therefore, a film forms.

Further, when the water that normally maintains a separation between the individual chains of food polymers has been evaporated, food polymers can be more crystalline and, therefore, less soluble. A specific example of this process is the retrogradation of starch. Retrogradation is a reaction that takes place in gelatinized starch when the amylose and amylopectin chains realign themselves, causing the liquid to gel. When native starch is heated and dissolves in water, the crystalline structure of amylose and amylopectin molecules is lost and they hydrate to form a viscous solution. If the viscous solution is cooled or left at lower temperature for long enough period, the linear molecules (e.g., amylose) and linear parts of amylopectin molecules retrograde and rearrange themselves again to a more crystalline structure, which is less soluble. Accordingly, if a food product in the container is warm and the lid on the container is cool (i.e., there exists a temperature gradient), evaporation of water from the product surface can occur and cause film formation.

The exact conditions for film formation are, however, not known. Although several methods have been used to test products for film formation potential, these methods have disadvantages and are not ideal for testing purposes. For example, temperature cycling using water circulation of hot and cold water and heat lamps have previously been used to study film formation. In both of these methods, temperature gradients were responsible for film formation. When temperature cycling with water circulation was used, however, several weeks were required for film formation. Slow film formation using temperature cycling was likely due to two different temperature gradients. In a first phase of cycling, a warm lid and a cool container were present. In a second phase, a cool lid and a warm container were present. Film that was formed under the first phase was subjected to condensed water vapor in the second phase. Therefore, film formation was slow under these conditions because a portion of the film was rehydrated before irreversibility occurred. Although such temperature cycling could occur during warehouse storage of the products, temperature cycling (as a laboratory method) is typically too slow and unpredictable. Additionally, previously known temperature cycling methods required products to be placed in a refrigerator for a certain amount of time (e.g., 24 hours), removed and placed in an incubator for a certain amount of time (e.g., 24 hours).

Such product transfer could not occur on the weekends and the products could remain in the refrigerator/incubator for up to 76 hrs. Therefore, these types of methods were also unreliable due to inaccurate protocols.

With respect to heat lamp film formation testing methods, the film forms more rapidly due to the constant temperature gradient. Heat lamps are not ideal for laboratory testing, however, because of the lack of temperature control and speed of the temperature ramp. Accordingly, previous film formation potential testing methods were either slow and/or lacked the ability to control the conditions.

Applicant has found an easy, predictable and fast method to detect film formation potential in food products packaged in containers. Specifically, Applicant has found that by preprogramming an incubator to simulate warehouse temperature cycles and conditions, Applicant is able to appropriately control the conditions that cause film formation in certain food products such as, but not limited to, baby food products. Indeed, simulation of warehouse conditions in a controlled, precise manner is important for studying film formation potential because not all warehouses that currently distribute film-forming foods (e.g., baby food, soup, pudding, etc.) have controlled temperatures, especially those located in warm temperature climates. As discussed above, the inability to control temperatures for food storage can cause the food products to be exposed to significantly fluctuating temperature, which causes temperature gradients that can cause film formation.

In contrast to previously used methods for testing film formation potential, using a programmable incubator allows for accurate and precise temperature control and duration, while providing the ability to test products over short periods of time (e.g., a weekend) and for extended amounts of time. Indeed, by using a programmable incubator, the food product can be exposed to accurate cycling schedule that can be adapted to simulate a variety of film-forming conditions (e.g., regional temperature fluctuations).

The methods of the present disclosure provide a temperature- and time-controlled incubator that can simulate the fluctuations in warehouse temperatures. This level of control provides for accurate simulation of conditions that can cause a temperature gradient between a lid of a container and the food product contained therein. The evaporation/condensation cycles that result from temperature cycling in the incubator deposit ingredient components (e.g., amylose and/or amylopectin from starch) onto the lid of the container or the surface of the food product. Over time, the material deposited on the lid of the container (or the surface of the food product) retrogrades, as discussed above, and forms a tough film that is objectionable.

The methods of the present disclosure include the use of incubators that may be preprogrammed to cycle through any number of different temperatures in any number of different amounts of times. For example, the incubators of the present disclosure may be capable of being programmed to cycle through temperatures ranging from about 0° C. to about 80° C. A temperature program of the present disclosure, therefore, may includes a temperature cycle from about 5° C. to about 40° C., or from about 10° C. to about 35° C., or from about 15° C. to about 30° C., or from about 20° C. to about 25° C. In an embodiment, an incubator is preprogrammed to cycle between about 10° C. and about 35° C.

The incubators of the present disclosure may also preprogrammed for temperature rise and fall times (e.g., temperature ramps). For example, the incubators may be preprogrammed to rise from an initial temperature to a higher temperature in an amount of time ranging from about 1 hour to about 12 hours, or from about 2 hours to about 10 hours, or from about 4 hours to about 8 hours, or in about 6 hours. The incubators may be preprogrammed to decrease from an increased temperature back to an initial temperature (or a temperature that is different than the initial temperature and the increased temperature) in the same, or a different, amount of time. In an embodiment, an incubator may be preprogrammed to rise from an initial temperature to a higher temperature in about 6 hours, and from the higher temperature to the initial temperature in about 6 hours.

Similarly, incubators used in the present methods may also be programmed to hold a specific temperature for a predetermined amount of time. The predetermined amount of time may range, for example, from about 1 to about 24 hours, or from about 2 to about 22 hours, or from about 4 to about 20 hours, or from about 6 to about 18 hours, or from about 8 to about 16 hours, or from about 10 to about 14 hours, or for about 12 hours.

Using the methods of the present disclosure, Applicant has been able to easily and accurately determine film formation potential in food products packaged in, for example, glass jars or plastic containers. In this regard, Applicant has been able to easily simulate warehouse temperatures by providing devices that consistently and accurately cycle temperatures that mimic actual warehouse conditions. Further, determination of the film formation potential in food products will result in more stable food products and reduction of consumer complaints.

The foregoing may be better understood by reference to the following Examples, which are presented for purposes of illustration and are not intended to limit the scope of the present disclosure.

EXAMPLES

Example 1

Applicant performed several experiments with a sample baby food product having a general composition similar to that disclosed in Table 1. During the experiments, the amounts and types of starch used were varied, as well as the amount of shear imposed on the product, in accordance with the starches disclosed in Table 2. When the starch level was increased in the formulation, the amount of water was reduced.

In the experiments, the baby food product was packaged in 4 ounce, glass jars with a metal PT closure. The glass jar dimensions were 2 5/16 inches by 2 9/16 inches. During mixing of the ingredients, a high shear kettle known as a APV multiverter was used to create high shear conditions. Instead of the multiverter, however, a skilled artisan will appreciate that other shearing devices may be used such as, but not limited to, a Breddo Likwifier. The filled jars were then placed into a preprogrammed incubator. The incubator was a stainless steel, preprogrammable incubator having shelves therein, twenty-four (24) interior cubic feet of space and a temperature range from about 4° C. to about 60° C. The incubator was preprogrammed to cycle between a temperature of about 10° C. to a temperature of about 35° C. over a time period of about twelve (12) hours (i.e., 6 hours to rise to 35° C. and 6 hours to fall to 10° C.).

During the temperature cycling, the product experienced enough temperature fluctuation to create a temperature gradient inside of the container that allowed for the coalescing of amylopectin from the food product. The amylopectin then retrograded and formed an irreversible film that looked like plastic or another similar material inside of the food container.

As shown by Table 2 above, and in view of the different types of starch, different amounts of starch, and different shear conditions used in the experiments, Applicant is now able to more easily, thoroughly, and quickly investigate potential reasons for film formation in packaged food products.

Example 2

Applicant performed several experiments with a sample baby food product having a general composition similar to that disclosed in Table 3 below. During the experiments, the amounts and types of starch used were varied, as well as the amount of shear imposed on the product, in accordance with the starches disclosed in Table 4, where "Y" represents the presence of film formation and "N" represents the lack of film formation. When the starch level was increased in the formulation, the amount of water was reduced.

TABLE 1

Composition of a Sample Food Product

| Ingredient | % Total Solids | Mass % | Solid % |
|---|---|---|---|
| Water | 0.00 | 54.080 | 0.000 |
| Mango Puree | 28.00 | 35.620 | 9.974 |
| Sugar (granulated) | 99.94 | 7.680 | 7.675 |
| Modified Waxy Corn Starch | 88.00 | 2.500 | 2.200 |
| Acid Citric Anhydrous | 99.50 | 0.065 | 0.065 |
| Vitamin C L-Ascorbic Acid (25 kg) | 100.00 | 0.050 | 0.050 |
| Mineral Premix (25 kg) | 95.50 | 0.005 | 0.005 |
| Total | | 100.000 | 19.968 |

TABLE 2

Test Results Using Modified Sample Food Products

| VARIABLE | PRODUCT WITH FILM | TOTAL | % FILM FORMER |
|---|---|---|---|
| Chemically Modified Waxy Corn Starch (4.5%), Low Shear | 0 | 2 | 0 |
| Chemically Modified Waxy Corn Starch (4.5%), High Shear | 0 | 0 | 0 |
| Chemically Modified Waxy Corn Starch (3.5%), Low Shear | 0 | 4 | 0 |
| Chemically Modified Waxy Corn Starch (3.5%), High Shear | 1 | 5 | 20 |
| Chemically Modified Waxy Corn Starch (2.5%), Low Shear | 0 | 6 | 0 |
| Chemically Modified Waxy Corn Starch (2.5%), High Shear | 1 | 4 | 25 |
| Physically Modified Waxy Corn Starch (3.5%), High Shear | 0 | 2 | 0 |
| Physically Modified Waxy Corn Starch (3.5%), Low Shear | 0 | 0 | 0 |
| Chemically Modified Tapioca Starch (1.5%), High Shear | 0 | 4 | 0 |
| Chemically Modified Tapioca Starch (1.5%), Low Shear | 3 | 3 | 100 |
| Chemically Modified Tapioca Starch (2.5%), Low Shear | 0 | 3 | 0 |
| Chemically Modified Tapioca Starch (2.5%), High Shear | 0 | 2 | 0 |
| Chemically Modified Tapioca Starch (3.5%), Low Shear | 0 | 5 | 0 |
| Chemically Modified Tapioca Starch (3.5%), High Shear | 1 | 4 | 25 |
| Unmodified Normal Corn Starch (3.5%), High Shear | 1 | 1 | 100 |
| Unmodified Normal Corn Starch (3.5%), Low Shear | 0 | 5 | 0 |
| Unmodified Waxy Corn Starch (3.5%), High Shear | 12 | 12 | 100 |
| Unmodified Waxy Corn Starch (3.5%), Low Shear | 6 | 12 | 50 |
| No Starch, High Shear | 1 | 1 | 100 |
| No Starch, Low Shear | 0 | 2 | 0 |
| Physically Modified Tapioca Starch (3.5%), High Shear | 2 | 2 | 100 |
| Physically Modified Tapioca Starch (3.5%), Low Shear | 0 | 0 | 0 |
| Xanthan, High Shear | 0 | 11 | 0 |
| Xanthan, Low Shear | 0 | 11 | 0 |
| Xanthan + Unmodified Normal Corn Starch, High Shear | 8 | 8 | 100 |
| Xanthan + Unmodified Normal Corn Starch, Low Shear | 3 | 10 | 30 |
| Xanthan + Non-Fat Dry Milk, High Shear | 11 | 11 | 100 |
| Xanthan + Non-Fat Dry Milk, Low Shear | 7 | 7 | 100 |

In the experiments, the baby food product was packaged in 4 ounce, glass jars with a metal PT closure. The glass jar dimensions were 2 5/16 inches by 2 9/16 inches. During mixing of the ingredients, a high shear kettle known as a APV multiverter was used to create high shear conditions. Instead of the multiverter, however, a skilled artisan will appreciate that other shearing devices may be used such as, but not limited to, a Breddo Likwifier. The filled jars were then placed into a preprogrammed incubator. The incubator was a stainless steel, preprogrammable incubator having shelves therein, twenty-four (24) interior cubic feet of space and a temperature range from about 4° C. to about 60° C. The incubator was preprogrammed to cycle between a temperature of about 10° C. to a temperature of about 35° C. over a time period of about twenty-four (24) hours (i.e., 11 hours to rise to 35° C., hold for 1 hour, and 11 hours to fall to 10° C.).

During the temperature cycling, the product experienced enough temperature fluctuation to create a temperature gradient inside of the container that allowed for the coalescing of amylopectin from the food product. The amylopectin then retrograded and formed an irreversible film that looked like plastic or another similar material inside of the food container.

TABLE 3

Composition of a Sample Food Product

| Ingredient | % Total Solids | Mass % | Solid % |
|---|---|---|---|
| Water | 0.00 | 54.080 | 0.000 |
| Mango Puree | 28.00 | 35.620 | 9.974 |
| Sugar (granulated) | 99.94 | 7.680 | 7.675 |
| Modified Waxy Corn Starch | 88.00 | 2.500 | 2.200 |
| Acid Citric Anhydrous | 99.50 | 0.065 | 0.065 |
| Vitamin C L-Ascorbic Acid (25 kg) | 100.00 | 0.050 | 0.050 |
| Mineral Premix (25 kg) | 95.50 | 0.005 | 0.005 |
| Total | | 100.000 | 19.968 |

TABLE 4

Test Results Using Modified Sample Food Products

| VARIABLE | 14-Jan | | 17-Jan | | 21-Jan | | 24-Jan | | 28-Jan | | 31-Jan | | 5-Feb | | 7-Feb | | 12-Feb | | 14-Feb | | 26-Feb | | 28-Feb | |
|---|---|---|---|---|---|---|---|---|---|---|---|---|---|---|---|---|---|---|---|---|---|---|---|---|
| | Y | N | Y | N | Y | N | Y | N | Y | N | Y | N | Y | N | Y | N | Y | N | Y | N | Y | N | Y | N |
| Chemically Modified Waxy Corn Starch (30 mi), High Shear | 0 | 4 | 0 | 4 | 0 | 4 | 0 | 4 | 0 | 4 | 2 | 2 | 1 | 3 | 2 | 2 | 1 | 3 | 1 | 3 | 0 | 4 | 1 | 3 |
| Chemically Modified Waxy Corn Starch (15 mi), High Shear | 0 | 4 | 0 | 4 | 0 | 4 | 1 | 3 | 2 | 2 | 2 | 2 | 4 | 0 | 4 | 0 | 1 | 3 | 4 | 0 | 2 | 2 | 3 | 1 |
| Chemically Modified Waxy Corn Starch (10 mi), High Shear | 0 | 4 | 0 | 4 | 2 | 2 | 2 | 2 | 3 | 1 | 1 | 3 | 3 | 1 | 0 | 4 | 2 | 2 | 1 | 3 | 2 | 2 | 2 | 2 |
| Unmodified Normal Corn Starch, High Shear | 4 | 0 | 2 | 2 | 1 | 3 | 4 | 0 | 4 | 0 | 4 | 0 | 4 | 0 | 4 | 0 | 4 | 0 | 3 | 1 | 3 | 1 | 4 | 0 |

As shown by Table 4 above, and in view of the different types of starch, different amounts of starch, and different shear conditions used in the experiments, Applicant is now able to more easily, thoroughly, and quickly investigate potential reasons for film formation in packaged food products.

It will be appreciated that the methods disclosed herein can be implemented using one or more computer programs or components. These components may be provided as a series of computer instructions on any conventional computer readable medium including, but not limited to, RAM, ROM, flash memory, magnetic or optical disks, optical memory, or other storage media. The instructions may be configured to be executed by a processor which, when executing the computer instructions, performs or facilitates the performance of all or part of the presently disclosed methods.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for testing at least one food product for film formation potential, the method comprising:
   providing a temperature-control device comprising a processor and a computer readable medium storing instructions which, when executed, cause the processor to cycle an interior temperature of the temperature-control device between at least three temperatures in a predetermined amount of time;
   placing a packaged food product in the temperature-control device; and
   causing the processor to execute the stored instructions, determining an amount of film formed on a surface selected from the group consisting of the food product, an interior lid on the packaged food product, an interior of the packaging, and combinations thereof; and wherein the stored instructions, when executed, cause the processor to cycle the interior temperature of the temperature-control device at least once.

2. The method according to claim 1 further comprising programming the computer readable medium to contain the stored instructions.

3. The method according to claim 1 wherein the stored instructions, when executed, cause the processor to cycle the interior temperature of the temperature-control device more than once.

4. The method according to claim 1 further comprising shearing the packaged food product before packaging.

5. The method according to claim 1 wherein a second cycle by the processor cycles the interior temperature of the temperature-control device between three temperatures, wherein at least one of the three temperatures of the second cycle is different from each of the at least three temperatures.

6. The method according to claim 1 wherein a subsequent cycle by the processor cycles the interior temperature of the temperature-control device between three temperatures, wherein at least one of the three temperatures of the subsequent cycle is different from each of the at least three temperatures of a previous cycle.

7. The method according to claim 1 wherein the temperature-control device is an incubator.

8. The method according to claim 1 wherein the packaged food product comprises starch.

9. The method according to claim 1 wherein the packaged food product is a food product selected from the group consisting of pudding, baby food, soup, and combinations thereof.

10. The method according to claim 1 wherein the predetermined amount of time ranges from about 6 hours to about 18 hours.

11. The method according to claim 1 wherein a first and a third temperature are the same temperature.

12. The method according to claim 1 wherein the packaged food product comprises starch, and a second packaged food product has an amount of starch that is different from an amount of starch in the packaged food product.

13. The method according to claim 1 wherein the packaged food product comprises starch, and the second packaged food product has a type of starch that is different from the starch in the packaged food product.

14. The method according to claim 1 wherein the packaged food product comprises starch, and more than one subsequent packaged food product, wherein each subsequent packaged food product has an amount of starch that is different from an amount of starch in the packaged food product, and any other subsequent packaged food product.

15. The method according to claim 1 wherein the packaged food product comprises starch, and more than one subsequent packaged food product, wherein each subsequent packaged food product has a type of starch that is different from the starch in the packaged food product, and any other subsequent packaged food product.

16. The method according to claim 1 wherein the method is simulating warehouse storage conditions of a food product.

17. The method according to claim 1 further comprising programming the computer readable medium to contain the stored instructions.

18. The method according to claim 1 wherein a subsequent amount of time is different from a previous amount of time.

19. The method according to claim 1 further comprising holding the interior temperature of the temperature-control device at any one of the at least three temperatures for a predetermined amount of time.

20. The method according to claim 1 further comprising removing the packaged food product from the temperature-control device after the cycling.

* * * * *